United States Patent [19]
Van Grinsven et al.

[11] Patent Number: 6,152,994
[45] Date of Patent: Nov. 28, 2000

[54] PROCESS FOR THE PURIFICATION OF AN ALKANOLAMINE

[75] Inventors: Petrus Franciscus Antonius Van Grinsven; Gijsbert Jan Van Heeringen, both of Amsterdam, Netherlands

[73] Assignee: Shell Oil Company, Houston, Tex.

[21] Appl. No.: 09/178,922

[22] Filed: Oct. 26, 1998

[30] Foreign Application Priority Data

Oct. 27, 1997 [EP] European Pat. Off. ............. 97203318

[51] Int. Cl.[7] .................................................. B01D 53/14
[52] U.S. Cl. ............................... 95/179; 95/193; 95/209; 203/42; 203/72
[58] Field of Search ................... 96/242, 234; 95/209, 95/193, 235, 236, 161, 163, 165, 166, 173, 174, 178, 179, 181, 183; 203/42, 72, 89

[56] References Cited

U.S. PATENT DOCUMENTS

| | | | |
|---|---|---|---|
| 2,668,748 | 2/1954 | Asbury | 95/161 |
| 2,729,588 | 1/1956 | Hannah | 95/179 |
| 3,664,930 | 5/1972 | Pottiez et al. | 95/193 |
| 3,739,548 | 6/1973 | Hegwer | 95/174 |
| 3,926,591 | 12/1975 | Wildmoser et al. | 95/183 |
| 4,035,166 | 7/1977 | Van Hecke | 95/163 |
| 4,152,217 | 5/1979 | Eisenberg et al. | 203/42 |
| 4,384,875 | 5/1983 | Batteux et al. | 95/166 |
| 4,504,449 | 3/1985 | Doerges et al. | 95/179 |
| 4,869,884 | 9/1989 | Riggs, Jr. | 95/183 |
| 5,108,551 | 4/1992 | Yan | 203/6 |
| 5,441,605 | 8/1995 | Beasley et al. | 203/42 |
| 5,820,837 | 10/1998 | Marjanovich et al. | 95/174 |

FOREIGN PATENT DOCUMENTS

| | | |
|---|---|---|
| 470004 | 2/1992 | European Pat. Off. . |
| 1572682 | 7/1980 | United Kingdom . |
| 2103645 | 2/1983 | United Kingdom . |

*Primary Examiner*—Duane S. Smith
*Attorney, Agent, or Firm*—Kim Muller

[57] ABSTRACT

A process for the purification of an aqueous alkanolamine which process involves subjecting the alkanolamine to a distillation process carried out in one or more film-type evaporators and involves at least two steps, wherein in the first step water is removed from the aqueous alkanolamine and in the second step the de-watered alkanolamine is further purified.

9 Claims, 1 Drawing Sheet

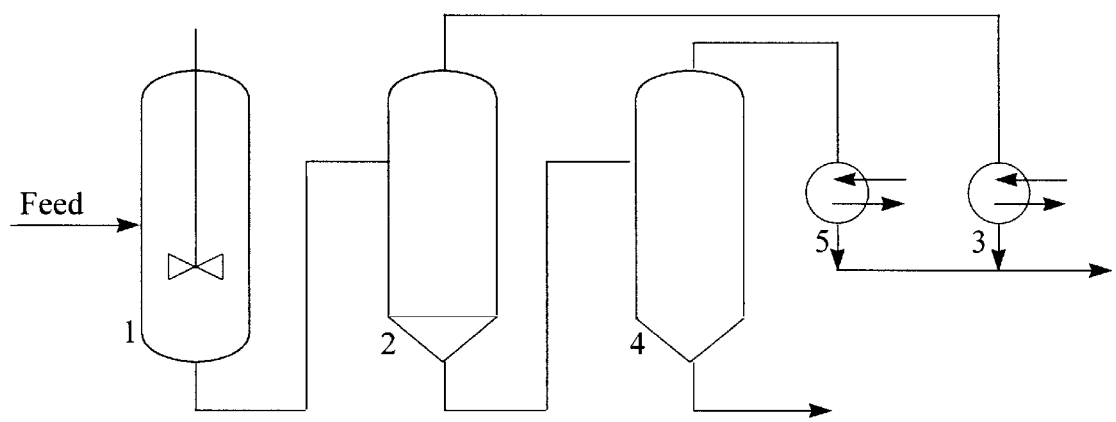

PROCESS FOR THE PURIFICATION OF AN ALKANOLAMINE

FIELD OF THE INVENTION

The present invention relates to a process for the purification of an aqueous alkanolamine, in particular one that is contaminated with degradation products.

BACKGROUND OF THE INVENTION

Alkanolamines are widely applied as solvents in the oil and chemical industry, for instance in absorption or extraction processes. Aqueous solutions of these compounds are much used to remove acidic compounds such as hydrogen sulphide or carbon dioxide from gas streams. Usually these removal processes are carried out regeneratively. This means that after the removal of acidic compounds from a gas stream by contacting the gas stream with a solvent in an absorption column at a relatively low temperature, yielding a purified gas and a so-called rich (or fat) solvent, the rich solvent is led to a regeneration column. There the rich solvent is heated and the acidic components are desorbed from the solvent, thus yielding an off-gas consisting of acidic components and a so-called lean solvent which may be recycled to the absorption column.

It is known that such solvents gradually degrade under the influence of heat, air, etc. So the heating applied during the regeneration, i.e. the desorption step, may cause some degradation. Also, certain absorbed acidic compounds may react with alkanolamines to form amine salts which are not desorbed from the alkanolamine by the heat in the regeneration column. In the art, such salts are generally called heat stable salts. Other contaminants often found are amides and oxazolidones. Oxazolidones may be formed by the reaction between an alkanolamine and carbon dioxide. For instance, the reaction of $CO_2$ with di-isopropanolamine yields 3-(2-hydroxypropyl)-5-methyl-2-oxazolidone (often just referred to as "oxazolidone"). In small concentrations such contaminants and degradation products do not present any operational problems, but in larger concentrations they do.

Firstly they cause a lowering of the molarity of the alkanolamine in the total solvent system and thus reduce the effectiveness of the absorption process. Furthermore it has been found that certain heat stable salts interfere with the normally occurring passivation of the carbon steel which is preferably employed for the absorption and regeneration columns and their internals and interconnections. This in turn causes corrosion and fouling by ferrous sulphide. Replacing the carbon steel by corrosion resistant steel is less attractive, for obvious cost reasons.

Another operational problem caused by heat stable salts and other contaminants in alkanolamine based solvent systems is foaming. The causes hereof are not yet completely understood, though it has been found that foaming occurs hardly or not at all if the solvent is clean. Many operators find it advantageous to monitor the concentration of the contaminants in the alkanolamine-water mixture, especially the heat stable salts, and to keep them at a low level, of e.g. less than 3000 ppm heat stable salts as anions.

In the past a commonly accepted practice was to continuously refresh a small part of the solvent stock, either voluntarily, by means of a bleed stream, or involuntarily, by means of solvent losses caused by small leaks or improper operation. Thus the concentration of contaminants hardly ever rose too high. However, such practices are becoming less and less acceptable, both from an environmental and from an economic point of view. Operators are striving more and more to reduce the number of solvent changes. Whereas maybe twenty years ago solvent stocks would be replaced at the rate of two up to ten inventories per year, nowadays solvent stock replacements of less than once every year are aimed for. However, at such low replacement rates it becomes increasingly necessary to control the degree of degradation and contamination.

The applicant has carried out extensive investigations into the problem of contamination of alkanolamines and how to deal with it. It was found in the first place that a proper operation of the absorption and regeneration processes, avoiding excessive (localised) heat inputs and ingress of air, is fundamental for minimising the formation of degradation products. Particularly to be avoided are oxygen, elemental sulphur, hydrogen cyanide and carbon disulphide. Nevertheless degradation and contamination still may occur, so there remains a need for a cheap, simple and effective purification process.

It has been proposed to clean contaminated, degraded alkanolamines by various processes, but so far, none of these has become very popular. For instance electro-dialysis has been proposed and is even offered on a commercial scale. So far this technique has not had much success as the cost thereof is about equal to a complete replacement of the solvent stock, especially if the amount of solvent is relatively small. Furthermore, it is known generally that membranes are vulnerable, both physically and chemically, and prone to plugging.

Another technique which is offered on a commercial scale, is ion exchange. This technique has not met with much success either, as it appears that it removes only acid contaminants so leaves in the heavy, high molecular weight, degradation products. Moreover, the process is not cheap either and produces a lot of wastewater, which is undesirable and sometimes difficult to dispose off.

So currently in most plants, when purification of the alkanolamine is required and gradual bleeding and replacing is not desired, a simple distillation, also known as thermal reclaiming, is employed using available on-site equipment such as distillation columns. This is especially suited to batch reclaiming processes. Dedicated thermal reclaimers are also known, for continuous reclaiming of a slip-stream, when the production of contaminants is high due to the particular composition of the acid gas stream being treated. However, in order to recover the valuable components as much as possible, long residence times must be employed. That in turn results in cracking of the bottom product, and consequently, in contamination of the reclaimer top product with light cracked species. It is to be noted that even when partial refluxing or recirculation of the aqueous alkanolamine takes place in the conventional thermal reclaimers, the process still should be considered as a single step process.

In UK patent specification No. 1,572,682 it is proposed to use steam distillation to remove oxazolidone from alkanolamines, but the residence times, in combination with the temperature of about 200 to 300° C. employed in that process, are unattractively high, resulting in the disadvantages explained above.

Neither do conventional vacuum distillation techniques using e.g. bubble-cap plate towers and tubular boilers fully satisfy, for the applicant found that also then unacceptable degradation may take place. Moreover, cost and heat economy remain problematic. Thus the general practice of trying to reclaim the aqueous alkanolamine in a conventional column, still or evaporator does not yield satisfactory results.

BRIEF DESCRIPTION OF THE DRAWING

The FIGURE shows components of an embodiment of the present invention.

DESCRIPTION OF THE INVENTION

The applicant has now surprisingly found that the disadvantages described above may be overcome by subjecting the contaminated aqueous alkanolamine to a distillation process which comprises at least two steps, wherein in the first step the aqueous alkanolamine is dehydrated (meaning that the alkanolamine is separated from the water) and in the second step the dehydrated alkanolamine is further purified using a special kind of distillation apparatus.

Accordingly the invention relates to a process for the purification of an aqueous alkanolamine which process comprises subjecting the alkanolamine to a distillation process, characterized in that the distillation process is carried out in one or more film-type evaporators and comprises at least two steps, wherein in the first step water is removed from the aqueous alkanolamine and in the second step the de-watered alkanolamine is further purified.

It may be noted that various conventional and vacuum distillation techniques are known from the literature, though not necessarily for industrial scale processes, let alone for the removal of degradation products commonly present in aqueous alkanolamines, such as heat stable salts, oxazolidones, amides, acids and the like.

Film-type evaporators are known per se and described in more detail in, for instance, Kirk-Othmer, Encyclopedia of Chemical Technology, third edition, New York, 1980, Volume 9, pages 478–481. This article discerns four main classes of film-type evaporators: the rising film or long-tube vertical evaporator, the falling-film evaporator, the horizontal-tube or spray-film evaporator, and the wiped-film or agitated-film evaporator, but does not suggest that any of these evaporators would be suitable for the (fractional) distillation process of the present invention.

The alkanolamine suitably has from 1 to four hydroxyl groups and from 2 to 30 carbon atoms. Examples of commercially applied extractants are diethanolamine, methylmethanolamine, methyldiethanolamine, di-isopropanolamine, diglycolamine, monoethanolamine, or mixtures thereof. Note that for the process of the present invention, the term alkanolamines should be interpreted broadly, and includes glycolamines. (Physical) co-solvents may be present such as sulfolane (tetramethylene sulfone).

The aqueous alkanolamine that is fed 1 to the first step of the process of the invention, is a mixture which may contain 10–90%, usually 25–75%, by mass of water, up to 20% by mass of contaminants and degradation products, the balance being alkanolamine and optional co-solvent. If sulfolane or another co-solvent is present, the mass ratio of this co-solvent to alkanolamine is usually in the order of 0.5 to 2.0.

In the first step the aqueous alkanolamine is dehydrated, which means that the bulk of the water is removed from the mixture. Preferably the conditions of the first step are chosen such, that more than 95%, especially more than 97%, of the water originally present is removed. The first step is suitably carried out a temperature in the range of 130 to 180° C. and a pressure in the range of 40 to 90 kPa (about 0.4 to 0.9 bar).

Obviously it is also possible to partially de-water the aqueous alkanolamine prior to subjecting it to the process of the present invention, by any process or device known per se not being a film type evaporator, but this is not preferred, as it is much simpler to carry out the dehydration in the single first step. It has been found possible that in the first step the aqueous alkanolamine is dehydrated in a falling film evaporator 2, and conventional components such as a condensor 3, which may be preferred for cost and efficiency reasons. However, also for cost and efficiency reasons it may be preferred to carry out the first step in the same equipment as wherein the second step is carried, which need not be a falling film evaporator, as will be explained below. Obviously it is also possible to partially de-water the aqueous alkanolamine prior to subjecting it to the process of the present invention.

Preferably in the second step the aqueous alkanolamine is further purified in an agitated-film evaporator 4, and conventional components such as a condensor 5, as this kind of equipment has given the best results for removing the heat stable salts and other contaminants, as well as any traces of water not removed in the first step. Thus in a suitable embodiment, also in the first step the aqueous alkanolamine is dehydrated in an agitated-film evaporator. It has furthermore been found by the applicant that especially in long term, continuous, operation of the process, the wiped film evaporator yields better results than the falling film evaporator in the first step. Suitably the second step is carried out a temperature in the range of 120 to 200° C. and a pressure in the range of 2 to 10 kPa (about 0.02 to 0.1 bar.

Suitably the process of the invention also comprises as an additional step the neutralisation of acidic compounds in the aqueous alkanolamine by addition of a stoichiometric amount of an inorganic base, such as sodium or potassium hydroxide. This addition may be carried out either before or after the first step.

The invention also relates to a process for the separation of acidic compounds such as $H_2S$ or $CO_2$ from an acidic gas stream which comprises the following steps:

a) contacting the acidic gas stream with an aqueous alkanolamine to yield a purified gas stream and a fat aqueous alkanolamine;

b) regenerating the fat aqueous alkanolamine by thermal desorption of the absorbed acidic compounds, to yield a lean aqueous alkanolamine and a stream of acidic compounds;

c) recycling the lean aqueous alkanolamine to step a);

d) reclaiming part of the aqueous alkanolamine by subjecting it to a process as described above, either continuously or batch-wise.

The invention is further illustrated by the following examples without restricting the scope of the present invention to these particular embodiments.

EXAMPLES

Example 1

A truckload of spent aqueous di-isopropanolamine was drawn off from the amine treating system of a European oil refinery. From this sample a few batches of 5 litres each were taken to analyse the composition, and to carry out preliminary tests at a laboratory scale, for finding the initial pilot plant conditions. The spent aqueous alkanolamine was then introduced into a stirred vessel of 200 litres for preheating, and fed at a rate of 100–170 kg/hr into a pilot plant unit comprising an agitated film evaporator having a capacity of about 200 kg/hr, and conventional auxiliary equipment such as pumps, coolers and the like.

During the trial runs, mass balances were made, and analysis for RFB (Regenerable Free Base, the amount of amine which can be liberated in the regenerator) and ATB (Actual Total Base, the amount of free amine (RFB) plus the amine bound to strong acidic components) were performed. The difference between the ATB and the RFB allows to calculate the amount of strong acids bound to the amine, i.e. of the amount of heat stable salts, expressed as meq/kg.

The composition of the feed is shown in Table I. In this and subsequent tables, the percentages do not add up exactly to one hundred, which is possibly due to small inaccuracies in the analyses and rounding-off errors.

TABLE I

| Di-isopropanolamine (ATB), % w | 41.7 |
|---|---|
| Water, % w | 54.6 |
| Oxazolidone + amides, % w | 3.1 |
| Heat stable salts, meq/kg | 285 |
| Total acids, meq/kg | 87 |

The organic acids were analysed to be mainly glycolic acid, formic acid, acetic acid and propionic acid. The main inorganic acids present caused the following anions to be found: $S_4^{2-}$, $Cl^-$, $NO_3^-$, $CN^-$ and $F^-$.

The aqueous di-isopropanolamine feed was split in two portions (examples 1a and 1b). The portion of example 1b was treated with a stoichiometric amount of caustic (NaOH) prior to step 1. About 0.28 eq/kg was required to obtain a pH-value of about 12, which is roughly equal to the difference between the ATB and the RFB. Each portion was treated batch-wise in two stages (the residue of the first step was used as feed for the second step) in the agitated thin film evaporator pilot plant, at the temperatures and pressures indicated in Table II. The results of the treatment after the second step are also indicated in Table II.

TABLE II

| Example # | 1a | 1b |
|---|---|---|
| Step 1 | | |
| temperature, ° C. | 159 | 154 |
| pressure, Kpa | 70 | 70 |
| Step 2 | | |
| temperature, ° C. | 155 | 177 |
| pressure, kPa | 2.5 | 5 |
| Alkanolamine recovery, % w | 91 | 96 |
| Mixed Products | | |
| Heat stable salts, meq/kg | 38 | 8 |
| Oxazolidone + amides, % w | 0.6 | 0.5 |

It can be seen that 91% of the originally present alkanolamine could be recovered whereas this figure increased to 96% by prior neutralization of the acids. Moreover it is shown that the amount of heat stable salts which was 87 meq/kg in the feed, can be more than halved, to 38 meq/kg, by applying a simple two step distillation process according to the invention, whereas prior neutralisation results in a further reduction, to 8 meq/kg.

Example 2

The experiments of example 1 were repeated with a truckload of contaminated solvent from a European natural gas treating plant operating the so-called Sulfinol-M process. Because this sample appeared to have a low acid content of its own, it was intentionally spiked with 5000 ppm of formic acid. The composition of the feed after spiking is given in Table III.

TABLE III

| Methyldiethanolamine (ATB), % w | 39.5 |
|---|---|
| Water, % w | 29.0 |
| Sulfolane, % w | 30.5 |
| Heat stable salts, meq/kg | 159 |

The results of the treatment after the second step are indicated in table IV.

TABLE IV

| Example # | 2a | 2b |
|---|---|---|
| Step 1 | | |
| temperature, ° C. | 148 | 143 |
| pressure, kPa | 70 | 70 |
| Step 2 | | |
| temperature, ° C. | 139 | 135 |
| pressure, kPa | 4 | 4 |
| Alkanolamine recovery, % w | 86 | 96 |
| Sulfolane recovery, % w | 82 | 91 |
| Mixed Products | | |
| Heat stable salts, meq/kg | 67 | 8 |

Example 3

The experiments of example 1 were repeated with a truckload of contaminated aqueous di-isopropanolamine from another European refinery suffering from a rather high HCN contamination problem. Rather than batch-wise, the experiment was carried out continuously, for 48 hours, employing a falling film evaporator for the first step and an agitated film evaporator for the second step. For comparison, also a test with an agitated film evaporator in the first step was carried out. The results were similar in that in all cases a recovery of more than 90% of the alkanolamine appeared to be feasible. However, though the consumption of energy of the falling film evaporator was less than that of the agitated film evaporator in the same stage, its performance was less: the distillate of the falling film evaporator still contained 25% w of di-isopropanolamine, compared to 2.2% w of di-isopropanolamine in the distillate of the agitated film evaporator.

Example 4

A mobile reclaimer unit consisting of two agitated-film evaporator units in series was built in four 20 ft containers, having a capacity of 600 to 1200 kg/hr. With this unit a complete inventory of 223 tonnes of solvent as present in a synthesis gas treating plant operating the so-called Sulfinol-M process was treated. The composition of the feed is given in table V.

TABLE V

| Methyldiethanolamine (ATB), % | 48.5 |
|---|---|
| Water, % w | 17 |
| Sulfolane, % w | 29.8 |
| High-boiling residue, % w | 4.7 |
| Heat stable salts, meq/kg | 97 |

The processing of the inventory was partly carried out on-line (while the gas treating unit was still in operation) and partly batch-wise. Sodium-hydroxide was added to the feed prior to the first distillation step. Distillation top products of the two stages were remixed and samples were taken regularly from feed products and residue, to establish removal efficiency for Heat Stable Salts and high-boiling products. Typical conditions and results are given in Table VI.

TABLE VI

| Step 1 | |
|---|---|
| temperature, ° C. | 120 |
| pressure, kPa | 75 |
| Step 2 | |
| temperature, ° C. | 170 |
| pressure, kPa | 5 |
| Alkanolamine recovery, % w | >95 |
| Sulfolane recovery, % w | >90 |
| Mixed Products | |
| Heat stable salts, meq/kg | 4 |
| High-boiling residue, % w | <0.5 |

During the batchwise production, some 30 tonnes of waste were produced out of 223 tonnes of feed. From this waste another 11 tonnes of sulfolane and methyldiethanolamine were recovered in a separate operation, increasing the overall recovery of alkanol amine and sulfolane to about 95%.

What is claimed is:

1. A process for the purification of an aqueous alkanolamine comprising:
   distilling the alkanolamine in one or more steps, the steps comprising:
   dehydrating the alkanolamine; and,
   further purifying the alkanolamine.

2. The process of claim 1, in which the alkanolamine is further purified in an agitated-film evaporator.

3. The process of claim 1, in which the alkanolamine is dehydrated in a falling film evaporator.

4. The process of claim 1, in which the alkanolamine is dehydrated in an agitated-film evaporator.

5. The process of claim 1, in which the distillation is carried out at a temperature in the range of 130° to 180° C. and a pressure in the range of 40 to 90 kPa.

6. The process of claim 1, in which the dehydration is carried out at a temperature in the range of 120° to 200° C. and a pressure in the range of 2 to 10 kPa.

7. The process of claim 1, in which the alkanolamine is selected from the group consisting of diethanolamine, methylmethanolamine, methyldiethanolamine, diisopropanol-amine, diglycolamine, monoethanolamine and mixtures thereof.

8. The process of claim 1, in which the alkanolamine is neutralized by addition of an inorganic base.

9. A process for the separation of acidic compounds from an acidic gas stream which comprises the following steps:
   a) contacting the acidic gas stream with an aqueous alkanolamine to yield a purified gas stream and a fat aqueous alkanolamine;
   b) regenerating the fat aqueous alkanolamine by thermal desorption of the absorbed acidic compounds, to yield a lean aqueous alkanolamine and a stream of acidic compounds;
   c) recycling the lean aqueous alkanolamine to step a);
   d) reclaiming part of the aqueous alkanolamine by subjecting it to a continuous or batch process comprising one or more steps, the steps comprising:
   dehydrating the alkanolamine; and,
   further purifying the alkanolamine.

* * * * *